US005325438A

United States Patent [19]

Browning et al.

[11] Patent Number: 5,325,438

[45] Date of Patent: Jun. 28, 1994

[54] ACTIVE NOISE-CANCELLATION SYSTEM FOR AUTOMOTIVE MUFFLERS

[75] Inventors: Douglas R. Browning, Randolph, N.J.; Michael A. Zuniga, Fairfax, Va.

[73] Assignee: AT&T Bell Laboratories, Murray Hill, N.J.

[21] Appl. No.: 11,566

[22] Filed: Feb. 1, 1993

[51] Int. Cl.[5] .......... A61F 11/06

[52] U.S. Cl. .......... 381/71; 181/206

[58] Field of Search .......... 381/71, 86, 94; 181/206

[56] References Cited

U.S. PATENT DOCUMENTS

| | | | |
|---|---|---|---|
| 5,046,103 | 9/1991 | Warnaka et al. | 381/94 |
| 5,097,923 | 3/1992 | Ziegler et al. | 381/71 |

FOREIGN PATENT DOCUMENTS

| | | | |
|---|---|---|---|
| 9115666 | 10/1991 | PCT Int'l Appl. | 181/206 |
| 1357330 | 6/1974 | United Kingdom | 181/206 |

*Primary Examiner*—Jin F. Ng
*Assistant Examiner*—P. W. Lee
*Attorney, Agent, or Firm*—Charles E. Graves; Martin I. Finston

[57] ABSTRACT

In an active control noise-cancelling muffler system, a substantially complete acoustic and mechanical decoupling of the noise-cancelling signal pipe from the gas exhaust pipe is achieved. The noise-cancelling signal delivery pipe is physically isolated and separate from the gas exhaust pipe, and is mounted separately. The outlet end of both pipes are essentially coplanar. Using pressure sensors on the tubes, the system also accurately and continuously electronically replicates the mixing of the exhaust noise and the noise-cancelling acoustic energy that goes on in the space immediately beyond the two outlets. This electronic signal is a useful alternative for a direct measure of the resultant two acoustic waves when they mix in the space beyond the tube outlets, and allows the system to continuously estimate the degree of success of noise cancellation without having to measure it directly when impractical. The system uses measures of pressure and temperature of the two tubes to continuously adjust a transducer drive signal that drives the sum of the pressures at the two tube outlets toward zero. An advantageous algorithm for the control process is identified.

9 Claims, 3 Drawing Sheets

ACTIVE NOISE-CANCELLATION SYSTEM FOR AUTOMOTIVE MUFFLERS

FIELD OF THE INVENTION

This invention relates generally to active cancellation of unwanted acoustic energy in a physical environment; and, more specifically, to improvements in active noise-cancelling automotive mufflers and muffler systems.

BACKGROUND OF THE INVENTION

Active noise-cancelling muffler systems used with internal combustion engines typically include means for monitoring selected parameters of the exhaust system and gas flow; and using the parameters, developing a noise-cancelling acoustic waveform. The "counter-acoustic wave" typically is formed first as an electrical waveform generated by a controller. The controller may be a computer or chip driver connected to an amplifier for a transducer that generates the cancelling signal. The cancelling wave and the exhaust gas energy continuously subtractively combine to effect the desired noise reduction.

In active noise-cancelling muffler systems, it is necessary to control the noise-cancelling acoustic signal both spatially and temporally so that the negative-going pulses of the cancelling wave coincide with the positive-going pulses of the exhaust gasses. The prior art teaches a variety of control strategies, using various physical structures to contain the transducer and launch the counter-acoustic wave. However, the physical design of the systems as well as the efficiency of the control signal leave much to be desired in terms of cost and reliability.

The controller requires accurate information as to the upstream exhaust gas reference pressure in order to generate a useful transducer input signal. One problem with many such systems of the prior art is that acoustic or mechanical coupling occurs between the counter-acoustic wave generator and the exhaust system of the IC engine. Readings of the exhaust gas reference pressure that are perturbed by mechanical or acoustical coupling from the noise cancelling apparatus, complicate the controller's function by requiring more complex and time-consuming computations to compensate for the perturbations. If the actual on-going reference gas pressure fluctuations is substantially obsecuted by such perturbation, the functionality of the system may be defeated altogether.

A continuously effective noise reduction system requires constant adjusting of the cancelling waveform to changing conditions which include exhaust temperature, frequency and amplitude. Ideally, despite the changing conditions, the exhaust gas acoustic energy is driven by the cancelling waveform toward zero at all times.

The degree of success in achieving full cancellation depends in part on continuously measuring the actual noise reduction occurring at the exhaust pipe outlet. The measurement of noise reduction is critical in determining controller inputs that will cause the transducer to continuously drive the exhaust gas noise to zero.

In most prior art active control noise-cancelling vehicular muffler systems, because the cancelling waveform and the exhaust noise waveform are acoustically and mechanically coupled in the same pipe, it is straightforward to measure the actual noise reduction simply by placing a single sensor at the common outlet. If, on the other hand, the noise-cancelling generator and the exhaust pipe are physically decoupled, the prior art expedient for measuring actual noise reduction is not available. Further, it is not practical for cost and reliability reasons to place a pickup microphone in the space beyond the exhaust pipe outlet to measure the actual reduced-noise exhaust gas amplitude. A practical measure of the spatial and temporal components of the noise-reduced exhaust gas pressure for use with decoupled systems is needed.

SUMMARY OF THE INVENTION

Substantially complete acoustic and mechanical decoupling of the noise-cancelling signal generating pipe from the gas exhaust pipe is achieved in accordance with the invention by providing a noise-cancelling signal delivery pipe which is entirely physically isolated and separate from the gas exhaust pipe. In one embodiment, the outlet end of the noise-cancelling pipe is placed side-by-side with the outlet end of the exhaust pipe. The noise-cancelling apparatus is a pipe closed at its far end where the transducer is mounted. The outlet end of this pipe advantageously is essentially coplanar with the outlet of the muffler exhaust pipe. The two pipes are closely spaced, but not directly mechanically coupled. The noise-cancelling pipe is formed to be as short as possible.

Additionally, a method and apparatus is used for accurately and continuously electronically mimicking the mixing of the exhaust noise and the noise-cancelling acoustic energy that goes on in the space immediately beyond the two outlets where the far-field acoustic cancellation takes place. Using this approach, a highly efficient noise-cancellation signal may be generated using any of several available algorithms. In accordance with this aspect of the invention, pressure sensors are respectively placed in the interior of the exhaust pipe and the noise cancellation tube, just inside the outlet mouths. By putting the two end sensors into the interior of the respective side-by-side tubes, there is high assurance that the respective pressure readings measure only the gas exhaust pressure and the noise cancellation signal pressure respectively. Neither reading is influenced by cross-coupling of the acoustic energy from the other. Further, ambient noise in the immediate environment has little, if any, effect on the readings.

The invention further contemplates using a computational algorithm, called the "filtered X least mean square" algorithm, which has been found to be uniquely adapted to calculating a noise-cancellation control signal, provided that the inputs of upstream reference pressure and the respective pressures at the outlet ports of the two tubes are continuously accurately inputted to the controller.

These and other features and advantages of the invention will be apparent from a reading of the detailed description to follow.

DETAILED DESCRIPTION OF ILLUSTRATIVE EMBODIMENT

Figure 1:
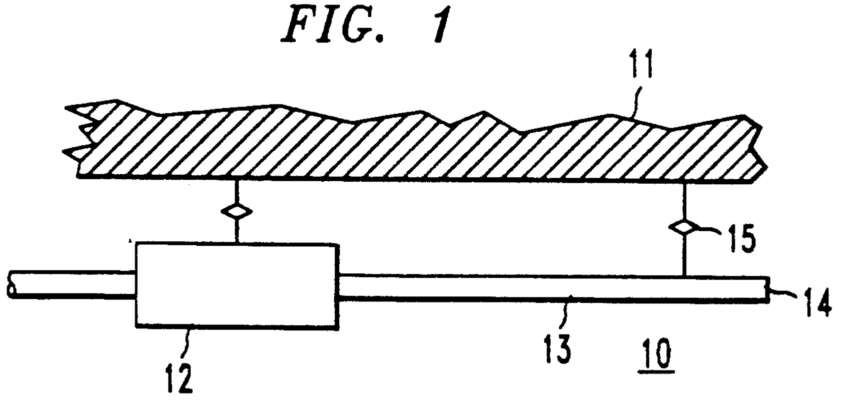
FIG. 1 is a schematic diagram of a general automotive exhaust apparatus.

As seen in FIG. 1, the exhaust system 1 of a typical automotive vehicle consists in part of a muffler 12 and a tail pipe 13 with an outlet 14. The system is mounted on the vehicle chassis, denoted 11 usually with noise isolation mounts 15.

Figure 2:
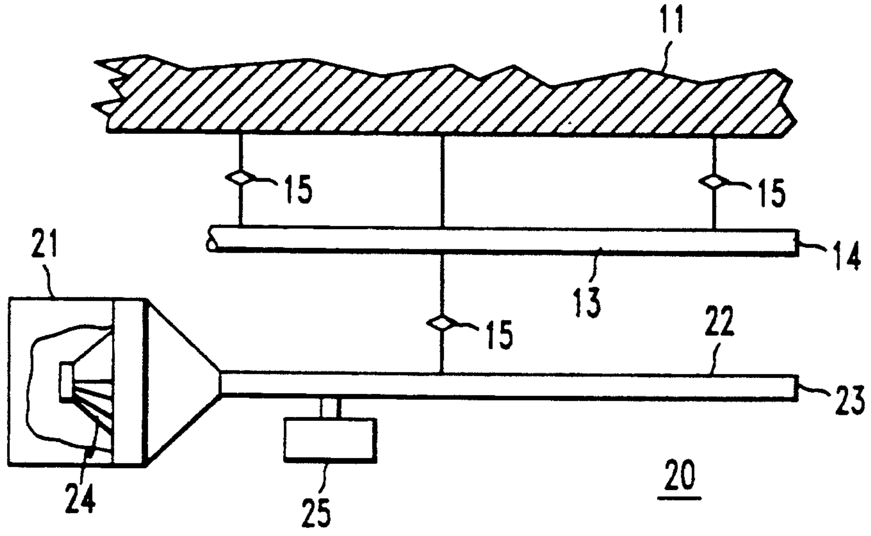
FIG. 2 is a schematic diagram of an automotive exhaust apparatus in accordance with the invention.

In accordance with the present invention, as seen in FIG. 2, a noise-cancelling system 20 consists of a closed end chamber 21 connected to a noise-cancelling tube 22, gas pressure sensors 16, 17, 18 a signal controller 30 and a transducer and amplifier 24, 40.

The tube 22 of the inventive system has an outlet 23. The two outlet ends 14, 23 are disposed closely adjacent to each other, advantageously in coplanar relation. Transducer 24 is mounted in the interior of the closed end of tube 22. Advantageously, a transducer with relatively little nonlinearity characteristic should be used in order to avoid introducing any distortion or harmonic content in the output which must be compensated for in generating the control signal. Additionally, the acoustic design of the combined closed-end chamber 21 and noise-cancelling tube 22 should be constructed to minimize the transmission of non-linear by-products of the transducer to the atmosphere through the tube exit 23.

Tube 22 and chamber 21 are connected to the vehicle chassis by isolation mounts 15 as in FIG. 1. In accordance with the invention, these mounts are the only mechanical or structural connection the noise-cancelling system 20 has with the exhaust system 10. That, and other expedients to be described, make the gas exhaust and the noise-cancelling systems substantially decoupled acoustically.

It is essential that the tube 22 be as free as possible of any acoustic energy other than the precise counter-acoustic waveform generated by transducer 24. Any resonances characteristic of the tube 22 may amplify small by significant harmonic acoustic energy produced by the transducer 24, and therefore are detrimental. To eliminate as much as possible the natural resonant frequencies in the tube 22, a suitably shaped acoustic cavity 25 connected to the tube 22 may be provided. However, by constructing the tube 22 to be less in length than about 0.25 meters, or more generally less than about one-half of the wavelength of the highest frequency to be cancelled, the resonances of tube 22 will occur at frequencies higher than those which are to be cancelled from the exhaust gas stream resonances.

Figure 3:
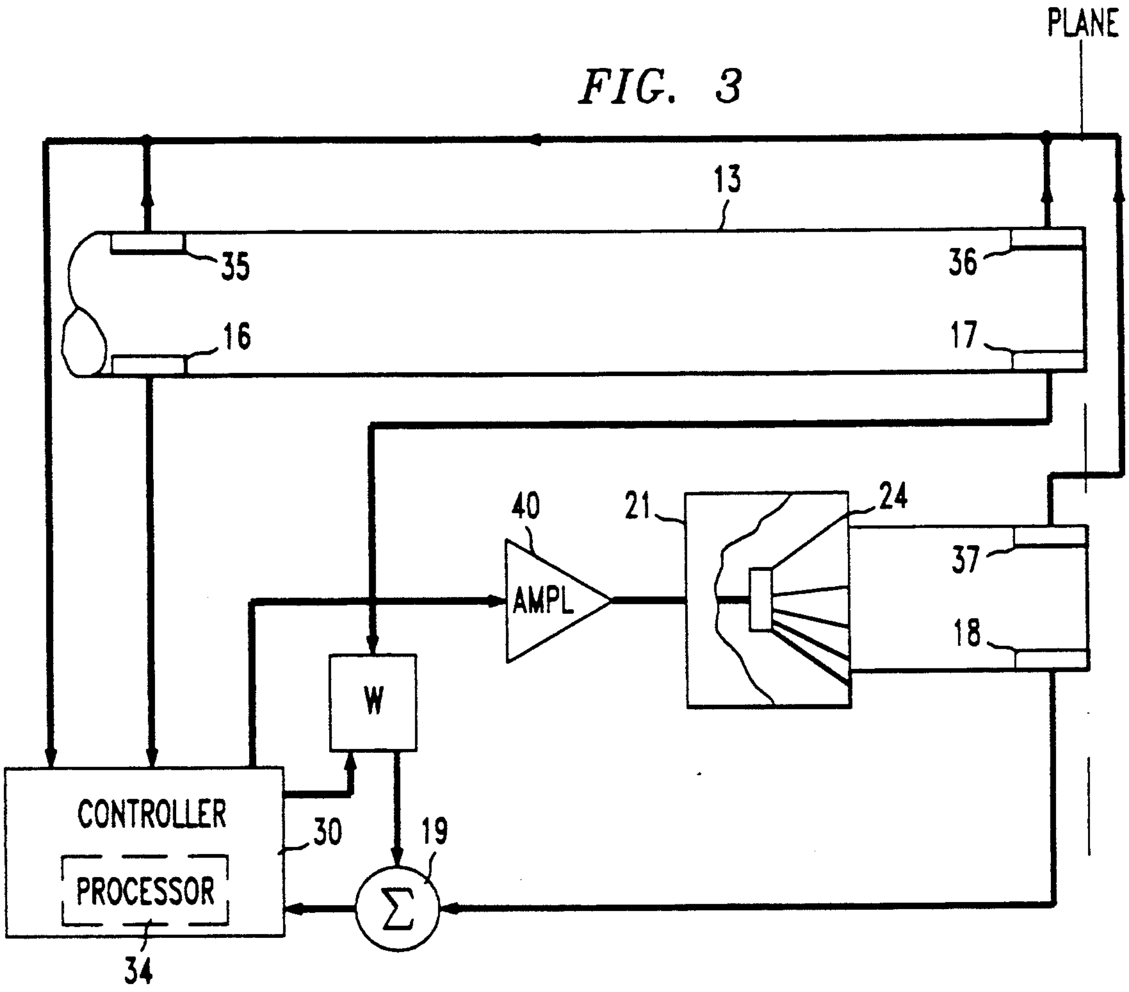
FIG. 3 is a schematic block diagram of the apparatus and noise-cancelling control system of the invention.

Referring now to FIG. 3, a first gas pressure sensor 16 is mounted upstream in the exhaust system 10 at a point forward of the exhaust outlet 14. That point should be located at a distance from the outlet which is greater in length than a half wavelength of the highest frequency to be eliminated. Sensor 16 provides an early and on-going measure of the exhaust gas wave in transit. A second exhaust gas pressure sensor 17 is mounted just inwardly of the outlet 14 of exhaust pipe 13. A third pressure sensor 18 is mounted just within the outlet 23 of delivery tube 22. The outputs of sensors 17 and 18, in accordance with one aspect of the invention, are electronically summed in summer 19. It may be useful to filter and weight the reading of sensor 17 in order to compensate for sound radiation differences due to temperature, gas flow, and diameters of the exhaust and noise-cancelling tubes, thereby improving the noise cancellation in the far field. The weighting may take place in an adjustment under the control of an operator; or the weighting may occur in the controller 30.

Controller 30 may comprise a computer or custom chip. It receives the output of summer 19 or alternatively the independent outputs of sensors 17 and 18 output of sensor 16. Controller 30 includes a digital signal processor or the equivalent to calculate the control signals to the amplifier 40 for the transducer based on the several inputs of gas pressure.

In fashioning the electrical input to amplifier 40, various inputs besides gas pressure may be desirable to take into account in controller 30, such as engine RPMs. In particular, temperature information can be critical for proper shaping of the counter-acoustic waveform. When the vehicle engine is first started, the exhaust gases are relatively cool; but, as the engine warms up or takes on load, the exhaust gases become intensely hot, reaching temperatures of several hundred to 1000 degrees F. at the pressure sensor 17. Of course, with elevated heat, the aforementioned filtering and weighting of the reading of sensor 17 is affected.

In accordance with of the invention, the noise-cancelling performance of the system 20 is improved by adding a temperature sensor 36 adjacent to pressure sensor 17 and a temperature sensor 37 adjacent to sensor 18. The temperature readings in conjunction with either measures of IC engine RPM or exhaust gas velocity, may be used to compute the weighting factor for the reading of sensor 17 to account for the sound radiation differences between the cancellation tube and the exhaust pipe. For identical tube diameters, this factor is a magnitude scaling term across the frequency band of interest; and may be experimentally determined for each engine exhaust and cancellation tube geometry. This factor is then included in the control algorithm as a table look-up value or as an empirical equation representing effects across the frequency range of interest.

Figure 4:
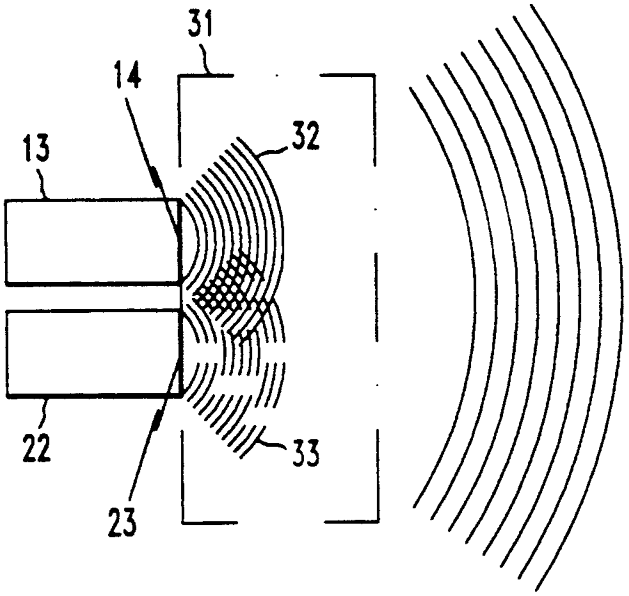
FIG. 4 is a diagram illustrating the mixing in space of a noisy and noise-cancelling waveform.
Figure 5:
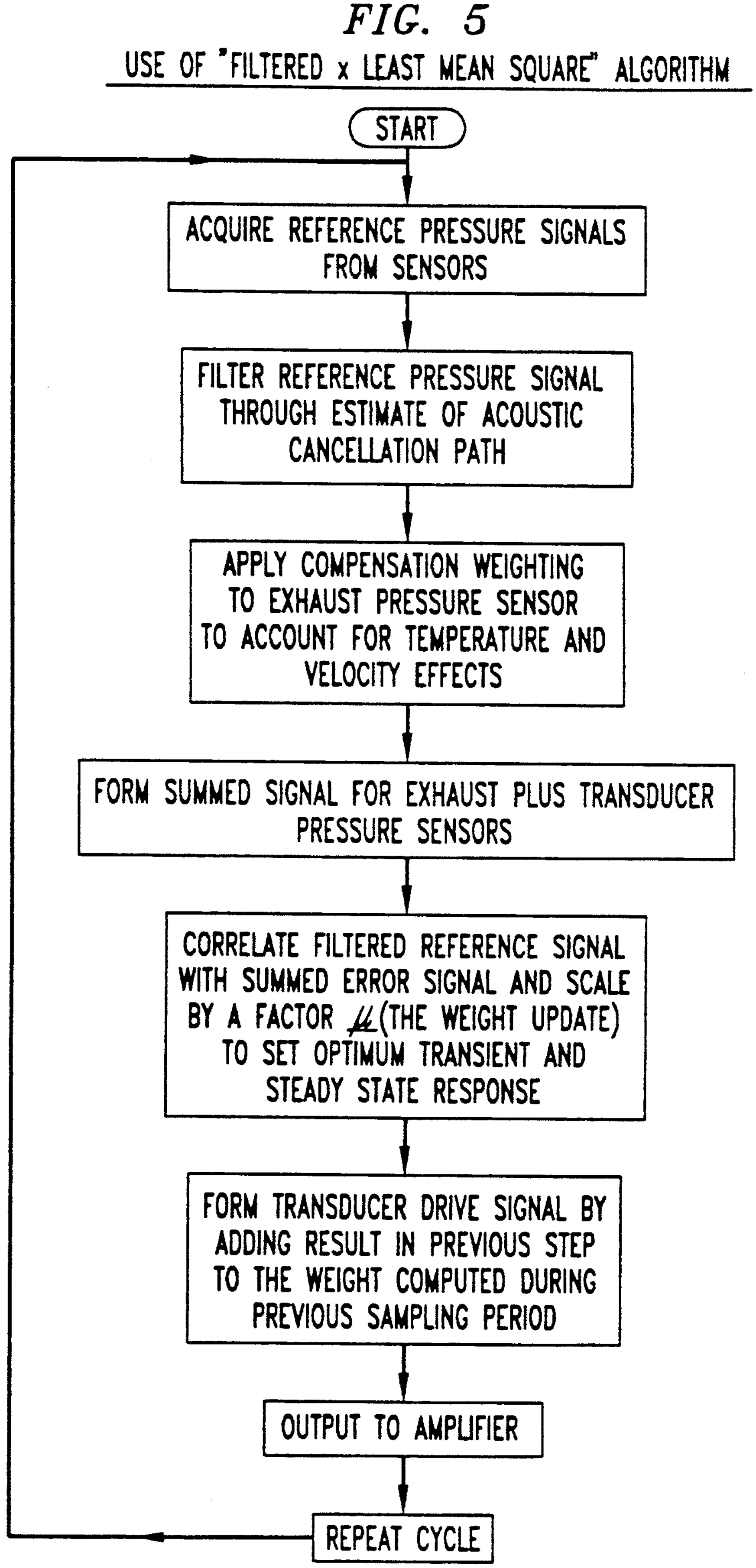
FIG. 5 is a flow chart illustrating the noise-canceling process of the invention.

Means in controller 30 are provided to vary the controller output as a function of the incoming readings of the value measured by summer 19. In accordance with the invention, this sum is maintained continuously at a minimum possible amount. As a result, as illustrated in FIG. 4, the acoustic mixing of the exhaust gas wave 32 and the counter-acoustic waveform 33 in the space denoted 31 immediately beyond the two outlets are substantially cancelling.

One strategy for continuously minimizing the value in summer 19 is to perform an algorithm in controller 30 known as the "filtered X last means square algorithm". This algorithm is fully described in Adaptive Signal Processing by B. Widrow and S. D. Stearns, pages Prentice Hall, Englewood Cliffs, N.J., 1985, pp. 288–297, and is hereby incorporated by reference.

The "filtered X" algorithm may be practiced in software written into, for example, a conventional digital signal processor 34 in controller 30. In practicing the filtered X-algorithm, the time advanced reference pressure detected by sensor 16 is sampled approximately every 250 microseconds. This signal is then filtered through a recursive, discrete-time filter representation of the acoustic cancellation path to form a filtered version of the pressure reference signal. The filtered reference is next correlated with the summed error signal for the current sample period, and scaled by a convergence gain factor $\mu$. This scaled, correlated signal becomes the adaptive weight update in the "filtered X" algorithm. From the weight update computation, the drive signal for transducer 24 is determined by adding the current weight update to the weight update computed for the previous sample period. This sum becomes the transducer drive signal that is fed to amplifier 40. The weight updating and resulting varying of the transducer driver signal is continuous.

Referring again to FIGS. 2 and 3, because of the substantial decoupling of the exhaust pipe 13 and the delivery tube 22, the readings picked up by pressure sensor 16 are uninfluenced by the output of transducer 24. As a result, it is not necessary in practicing the algorithm in controller 30 to take into account any modulations of the gas exhaust energy caused by the noise-cancelling wave. Further, the isolation of the two tubes allows controller 30 to track slow changes in the transfer function of the noise-cancelling tube much more simply than if the two tubes were directly mechanically coupled.

By accessing either the output of the noise-cancelling tube sensor 18 before the signal enters the summer 19 or the output of the summer 19 and the output of controller 30, a reliable and continuous on-line estimate of the noise-cancelling tube transfer function can be made without interference from the exhaust noise. This is an advantage over some prior art automotive exhaust noise-cancelling systems which use a pilot signal to identify this transfer function in order to enable the noise-cancelling signal to be responsive to changes in the characteristics of the delivery tube. A pilot signal necessarily adds further noise to the system output, however, which is counter to the purpose of noise-cancelling muffler systems.

It also may be desirable to monitor the temperature in the noise-cancelling tube to aid in the on-line estimation of the transfer function characteristics of the noise-cancelling tube. In accordance with the invention, the monitored temperature information of the noise-cancelling tube may be used to select, from a library 38 of predetermined transfer functions contained in a database in controller 30, an initial estimate of the transfer function appropriate for the current measured temperature. This expedient is an effective way to initiate running the algorithm; and has the advantage of providing more rapid estimation of the required transfer function than could otherwise be achieved without the temperature measurement.

A further advantage of the acoustic isolation and separation of the exhaust pipe 13 and the tube and 22, is that temperature excursions occurring in the exhaust pipe at least do not require instantaneous compensating adjustment of the transducer 24 amplitude or phase due to effects of exhaust gasses on the acoustic cancellation path transfer function, as would be the case if the delivery tube were directly mechanically coupled into the exhaust pipe.

Figure 6:
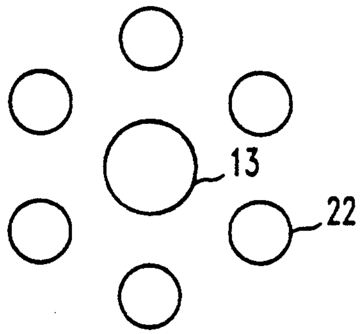
FIG. 6 is a second physical arrangement of plural separate noise-cancelling tubes in relation to the exhaust pipe.

The principles of the invention have been illustrated by the example of a single noise-cancelling tube mounted to the side of the gas exhaust. However, the principles are applicable to substantially any configuration of noise-cancelling tubes. One such variation is shown in FIG. 6, as a series of noise-cancelling tubes 22 symmetrically arrayed around the gas exhaust pipe 13. Further configurations can readily be envisioned by persons skilled in the art.

We claim:

1. In an internal combustion engine exhaust gas system comprising an exhaust pipe having an outlet, apparatus for reducing the acoustic energy in the exhaust stream at said outlet comprising:

a noise-cancelling signal delivery tube, said delivery tube being separate from but located adjacent to said exhaust pipe and having its outlet disposed adjacent to said exhaust pipe outlet;

a transducer mounted in the end of the delivery tube opposite the delivery tube outlet for generating an exhaust gas noise-cancelling signal;

first and second gas pressure sensors respectively mounted at the outlet ends of said exhaust pipe and said delivery tube;

a third gas pressure sensor mounted upstream in said exhaust pipe for generating a pressure reference signal;

means responsive to readings from said first and second gas pressure sensors for generating an electronic composite signal replicating the combined waveform of the exhaust noise and noise-cancelling waveforms in the space immediately beyond said tube outlets; and means responsive to readings from said third sensor and to said composite signal for generating a drive signal for said transducer, such that the composite signal tends toward a minimum value, corresponding to at least partial cancellation of exhaust noise.

2. Apparatus in accordance with claim 1, wherein said composite signal generating means further comprises means for summing the readings of said first and said second pressure sensors, and said apparatus further comprising:

means for periodically spatially and temporally adjusting said transducer drive signal to a level that maintains the resulting sum at a minimum value.

3. Apparatus in accordance with claim 2, wherein said first and second pressure sensors are respectively placed in the interior of said exhaust pipe and said delivery tube at said tube outlets.

4. Apparatus in accordance with claim 3, wherein said respective exhaust pipe and delivery tube outlet ends are disposed adjacent to each other and are in substantial co-planar relation.

5. Apparatus in accordance with claim 4, wherein the length of the delivery tube is approximately one-half the wavelength of the highest frequency present to be cancelled in said exhaust stream, and said length is to be measured from the delivery tube end where the transducer is mounted to the delivery tube outlet.

6. Apparatus in accordance with claim 5, wherein said means for generating said transducer drive signal further comprises:

means for periodically sampling said pressure reference signal;

means for filtering said sample through a recursive, discrete-time filter representation of the acoustic cancellation path, thereby to form a filtered version of said pressure reference signal;

means for correlating the filtered version of said pressure reference signal with the sum of said first and second pressure sensor readings for the current sample period, and scaling the result by a convergence gain factor to create a current weight update number; and means for currently adjusting the drive signal for said transducer by adding the current weight update number to the weight update number computed for the previous sample period.

7. Apparatus in accordance with claim 6, further comprising:

a first temperature sensor disposed adjacent to said first pressure sensor and a second temperature sensor disposed adjacent to second pressure sensor; and means responsive to the readings from said temperature sensors for adjusting the drive signal of said transducer to continue to drive said sum of said first and said second pressures to minimum value.

8. Apparatus in accordance with claim 7, further comprising:

a database of pre-determined transfer functions;

means responsive to the temperature reading from said second temperature sensor for selecting from said database an estimate of the transfer function appropriate for the current measured temperature; and means for using the selected, estimated transfer function to further adjust said transducer drive signal.

9. Apparatus in accordance with claim 7, wherein:

(a) said delivery tube, to be referred to as the first delivery tube, is part of a symmetrical array disposed around the exhaust pipe; and (b) the array includes at least one additional noise-cancelling signal delivery tube adapted to cooperate with the first delivery tube for at least partially cancelling exhaust noise.

* * * * *

UNITED STATES PATENT AND TRADEMARK OFFICE

CERTIFICATE OF CORRECTION

PATENT NO. : 5,325,438

DATED : June 28, 1994

INVENTOR(S) : Douglas R. Browning and Michael A. Zuniga

It is certified that error appears in the above-indentified patent and that said Letters Patent is hereby corrected as shown below:

Column 2, line 14: Change "generating pipe" to --generating tube--.

Column 2, line 17: Change "pipe" to --tube--.

Column 2, line 19: Change "pipe" to --tube--.

Column 2, line 21: Change "pipe closed" to --tube closed--.

Column 2, line 23: Change "pipe" to --tube--.

Column 2, line 25: Change "pipes" to --tubes (i.e., the exhaust pipe and the noise-cancelling signal delivery tube)--.

Column 2, line 26: Change "pipe" to --tube--.

Column 3, line 11: Change "tail" to --exhaust--.

UNITED STATES PATENT AND TRADEMARK OFFICE

CERTIFICATE OF CORRECTION

PATENT NO. : 5,325,438
DATED : June 28, 1994
INVENTOR(S) : Douglas R. Browning and Michael A. Zuniga It is certified that error appears in the above-indentified patent and that said Letters Patent is hereby corrected as shown below:

Column 3, line 31: Change "tube exit" to --outlet--.

Column 5, line 51: Change "tube and 22" to --tube 22--.

Column 6, line 22: Delete "said".

Column 6, line 23: Change "tube outlets" to --the outlets of said exhaust pipe and said delivery tube--.

Column 6, line 41: Change "said tube outlets" to --the outlets of said exhaust pipe and said delivery tube--.

In the abstract, line 3: Change "pipe" to --tube--.

In the abstract, line 5: Change "pipe" to --tube--.

In the abstract, line 7: Change "pipes" to --tubes (i.e., the exhaust pipe and the signal delivery tube)--.

Signed and Sealed this

Thirty-first Day of January, 1995

*Attest:*

BRUCE LEHMAN

*Attesting Officer*

*Commissioner of Patents and Trademarks*